United States Patent
Bäck

(10) Patent No.: US 9,220,639 B2
(45) Date of Patent: Dec. 29, 2015

(54) BOXER SHORTS FORMED BY A METHOD WHICH DOES NOT REQUIRE REMOVAL OF MATERIAL FROM THE MANUFACTURING WEB

(75) Inventor: Lucas Bäck, Billdal (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 931 days.

(21) Appl. No.: 13/381,715

(22) PCT Filed: Jul. 16, 2009

(86) PCT No.: PCT/SE2009/000370
§ 371 (c)(1),
(2), (4) Date: Dec. 30, 2011

(87) PCT Pub. No.: WO2011/008138
PCT Pub. Date: Jan. 20, 2011

(65) Prior Publication Data
US 2012/0123377 A1    May 17, 2012

(51) Int. Cl.
*A61F 13/15* (2006.01)
*A61F 13/20* (2006.01)
*A61F 13/496* (2006.01)

(52) U.S. Cl.
CPC ..... *A61F 13/15739* (2013.01); *A61F 13/15699* (2013.01); *A61F 13/496* (2013.01); *A61F 13/4963* (2013.01)

(58) Field of Classification Search
USPC ........... 604/385.24–385.25, 385.01, 393–395
See application file for complete search history.

(56) References Cited

U.S. PATENT DOCUMENTS

| 4,280,230 | A | * | 7/1981 | LaFleur | 2/408 |
| 5,930,838 | A | * | 8/1999 | Carter-Scott-Pomije | 2/79 |
| 6,193,702 | B1 | | 2/2001 | Spencer | |
| 6,336,923 | B1 | | 1/2002 | Fujioka et al. | |
| 6,807,685 | B1 | * | 10/2004 | Hasegawa et al. | 2/406 |
| 7,047,572 | B2 | * | 5/2006 | Hopkins | 2/400 |
| 2003/0115660 | A1 | | 6/2003 | Hopkins | |
| 2004/0098791 | A1 | | 5/2004 | Faulks | |
| 2006/0191059 | A1 | * | 8/2006 | Smith | 2/400 |

FOREIGN PATENT DOCUMENTS

| EP | 1 035 818 | 4/2002 |
| JP | H06 57502 A | 3/1994 |
| JP | 2004-159949 A | 6/2004 |
| WO | 2006/038946 | 4/2006 |
| WO | 2008/037281 | 4/2008 |
| WO | 2008/123348 | 10/2008 |

OTHER PUBLICATIONS

Extended European search report dated Oct. 23, 2013 for European application No. 09 84 7406.7 (5 pages).

* cited by examiner

*Primary Examiner* — Michele M Kidwell
(74) *Attorney, Agent, or Firm* — Drinker Biddle & Reath LLP

(57) ABSTRACT

A pant-type article having a boxer-short configuration. The article includes first and second panels which are joined via a crotch region joining. Folding and inverting the panels, and sealing along side-seams and inner legs seams provides a boxer-short. Methods for manufacturing the pant-type article are also provided. The pant-type article can be manufactured in a continuous side-by-side fashion.

9 Claims, 7 Drawing Sheets

BOXER SHORTS FORMED BY A METHOD WHICH DOES NOT REQUIRE REMOVAL OF MATERIAL FROM THE MANUFACTURING WEB

CROSS-REFERENCE TO PRIOR APPLICATION

This application is a §371 National Stage Application of PCT International Application No. PCT/SE2009/000370 filed Jul. 16, 2009, which is incorporated herein in its entirety.

TECHNICAL FIELD

The present disclosure provides a pant-type article, particularly boxer-shorts. The disclosure also provides methods for producing such articles.

BACKGROUND

Pant-type articles are used as regular pants (underwear), protective pants and absorbent pants. A large number of different methods for producing such articles are known.

A recurring problem with pant manufacture (particularly absorbent pants) has been that pants having a "boxer-short" configuration have been difficult to manufacture efficiently. A simple way to manufacture boxer-short pants is to join front and rear panels, and remove portions of the material in the crotch portion to form the legs (as per US 2003/0115660). However, in these methods, the material which is removed in the crotch portion is discarded, which often requires extra handling steps to deal with the waste material. In addition, the process shown in US 2003/0115660 makes it difficult to apply core packets to the pants.

It is desirable to manufacture pant-type articles side-by-side in a continuous process, in which front and rear halves are constituted by two separate material webs which are joined at the crotch portion and folded together such that front and rear halves overlap. Sealing and cutting the webs provides individual articles. Side-by-side processes are desirable, as they allow rapid, efficient production, while also allowing front and rear halves to be varied independently of one another e.g. in their size, shape, properties or materials. Such variation is not possible in so-called "head-to-tail" manufacture, in which front and rear halves are cut from the same material web.

However, any attempt to manufacture pants using known side-by-side processes will not allow leg holes to extend beyond the fold-line, as is required in boxer-shorts. This is due to the lack of material beyond the fold-line that can form legs.

There remains, therefore, a need for a new pant-type article, and associated manufacturing method, particularly articles having a boxer-short configuration. The pant-type article should be simple and easy to construct and minimize wastage. The pant-type article should provide advantages in strength, comfort and leakage-prevention as compared with known pant-type articles.

SUMMARY

Accordingly, a first aspect relates to a pant-type article, said article including a first panel and a second panel. The first and second panels are joined by first and second side seams to form a waist opening at a first transverse end of said article. The first and second panels are further joined by a crotch region joint in a crotch region spaced from said waist opening to thereby form a pair of leg openings at a second transverse end of said article.

The crotch region joint includes a crotch seam extending substantially perpendicular to said first and second side seams and spaced therefrom, said crotch seam having a first end and a second end. The crotch region joint further includes a first inner leg seam extending a first distance (W) from the first end of the crotch seam to the second transverse end of the article, and a second inner leg seam extending said first distance (W) from said second end of said crotch seam to said second transverse end of said article. The article has an interior and an exterior. The article further includes a crotch flap located in the interior of said article, said crotch flap including material of said first and second panels.

According to an embodiment, the crotch flap extends from said crotch seam by a second distance (W') substantially equal to said first distance (W).

The first and second panels may be joined in said crotch flap, at least along longitudinal edges thereof. The crotch flap may also be joined to the inside face of said first or said second panel. The pant-type article may additionally include an absorbent member located on the interior of the article, at least in the crotch region thereof.

Suitably, the first and second inner leg seams are arranged parallel to the side seams of the article. Alternatively, the first and second inner leg seams are not parallel to one another. In particular, the first and second inner leg seams may be further from one another at the point at which they meet the crotch seam than at the leg openings.

A further aspect relates to a first method for manufacturing a pant-type article, said method including the steps of:

a. providing a first panel said first panel having an extension in the transverse direction (T) and being defined by first and second longitudinal edges and having an extension in the longitudinal direction (L) and being defined by first and second transverse edges; said first panel also having opposing inside and outside faces;

b. providing a second panel, said second panel having an extension in the transverse direction (T) and being defined by first and second longitudinal edges and having an extension in the longitudinal direction (L) and being defined by first and second transverse edges; said second panel also having opposing inside and outside faces;

c. bringing the first and second panels to overlap with one another, such that their outside faces face one another;

d. joining said first and second panels to form a crotch seam extending substantially parallel to said first and second transverse edges and spaced therefrom;

e. joining said first and second panels to form a first inner leg seam extending a first distance (W) from a first end of said crotch seam to a first transverse edge of said first and second panels;

f. joining said first and second panels to form a second inner leg seam extending said first distance (W) from a second end of said crotch seam to a first transverse edge of said first and second panels;

g. cutting the first and second panels along two lines, each of which extends from the first transverse edge of the first and second panels to the crotch seam so as to define a crotch flap;

h. folding the co-joined first and second panels along the crotch seam; so that the inside faces of said first and second panels face one another;

i. inverting the co joined first and second panels in the region between the inner leg seams and respective longitudinal edges of the panels to form leg openings; and j. joining the first and second panels together along first and second longitudinal edges to define side seams.

Step g. can take place at any point after step b, but before step h.

Steps e., f. and j. can take place at any point after step c.

The method above provides a pant-type article.

The method may further include the step of joining first and second panels to one another in said crotch flap at least along longitudinal edges thereof. It may further include the step of joining said crotch flap to the inside face of said first or said second panel. Steps d., e. and f. of the method may be carried out essentially simultaneously in the same joining step. First and second panels may be cut such that one cutting line lies within each of the first and the second inner leg seam. To make an absorbent pant-type article, the method could include the step of incorporating an absorbent member in the interior of the article, at least in the crotch region thereof.

Another aspect relates to a second method for manufacturing a pant-type article, said method including the steps of:

a. providing a first web, said first web having a major extension in the machine direction (MD) and a minor extension in the cross direction (CD); said first web being defined in the machine direction (MD) by first and second transverse edges and having opposing inside and outside faces;

b. providing a second web, said second web having a major extension in the machine direction (MD) and a minor extension in the cross direction (CD); said second web being defined in the machine direction (MD) by first and second transverse edges and having opposing inside and outside faces;

c. bringing the first and second webs to overlap with one another, such that their outside faces face one another;

d. joining said first and second webs together at regular intervals in the machine direction to form a plurality of crotch seams extending substantially in the machine direction (MD) and spaced from first and second transverse edges of each web; each crotch seam having a first end and a second end;

e. joining said first and second webs together at regular intervals in the machine direction to form a plurality of first inner leg seams extending a first distance (W) from the first end of each crotch seam to a first transverse edge of each web;

f. joining said first and second webs together at regular intervals in the machine direction to form a plurality of second inner leg seams extending said first distance (W) from the second end of each crotch seam to a first transverse edge of each web;

g. cutting the first and second webs along pairs of lines spaced at regular intervals in the machine direction, each pair of lines extending from the first transverse edge of each web to each crotch seam so as to define a plurality of crotch flaps h. folding the co-joined first and second webs along the crotch seams; so that the inside faces of said first and second webs face one another;

i. inverting the co joined first and second webs in the region between first and second inner leg seams to define leg openings;

j. joining the first and second webs together in said inverted region from the first to the second transverse edge of each web such that leg seams are provided;

k. cutting each first and second web within the leg seams from the first to the second transverse edge of each web; so as to provide individual pant-type articles.

Steps e. f. and g. can take place in any order after step c, but before step h.

Step j. can take place at any point after step c.

The method may further include the step of joining first and second webs to one another in each crotch flap, at least along longitudinal edges thereof. Additionally, the method may also include the step of joining said crotch flap to the inside face of said first or said second web. Suitably, steps d., e. and f. are carried out essentially simultaneously in the same joining step. First and second webs may be cut such that one cutting line lies within each of the first and the second inner leg seams. To provide an absorbent pant-type article, the method may further include the step of incorporating an absorbent member in the interior of the article, at least in the crotch region thereof.

DEFINITIONS

"Boxer-shorts" are distinguished from other pant-type articles in that they have well-defined leg portions which extend at least partly along the inside of the wearer's legs, rather than just leg-openings. Unlike other types of underwear, they have well-defined leg seams which are located on the inside leg of the wearer in use. In other words, boxer-shorts extend from the crotch portion in a direction away from the waist opening.

DETAILED DESCRIPTION OF PREFERRED EMBODIMENTS

Figure 1:
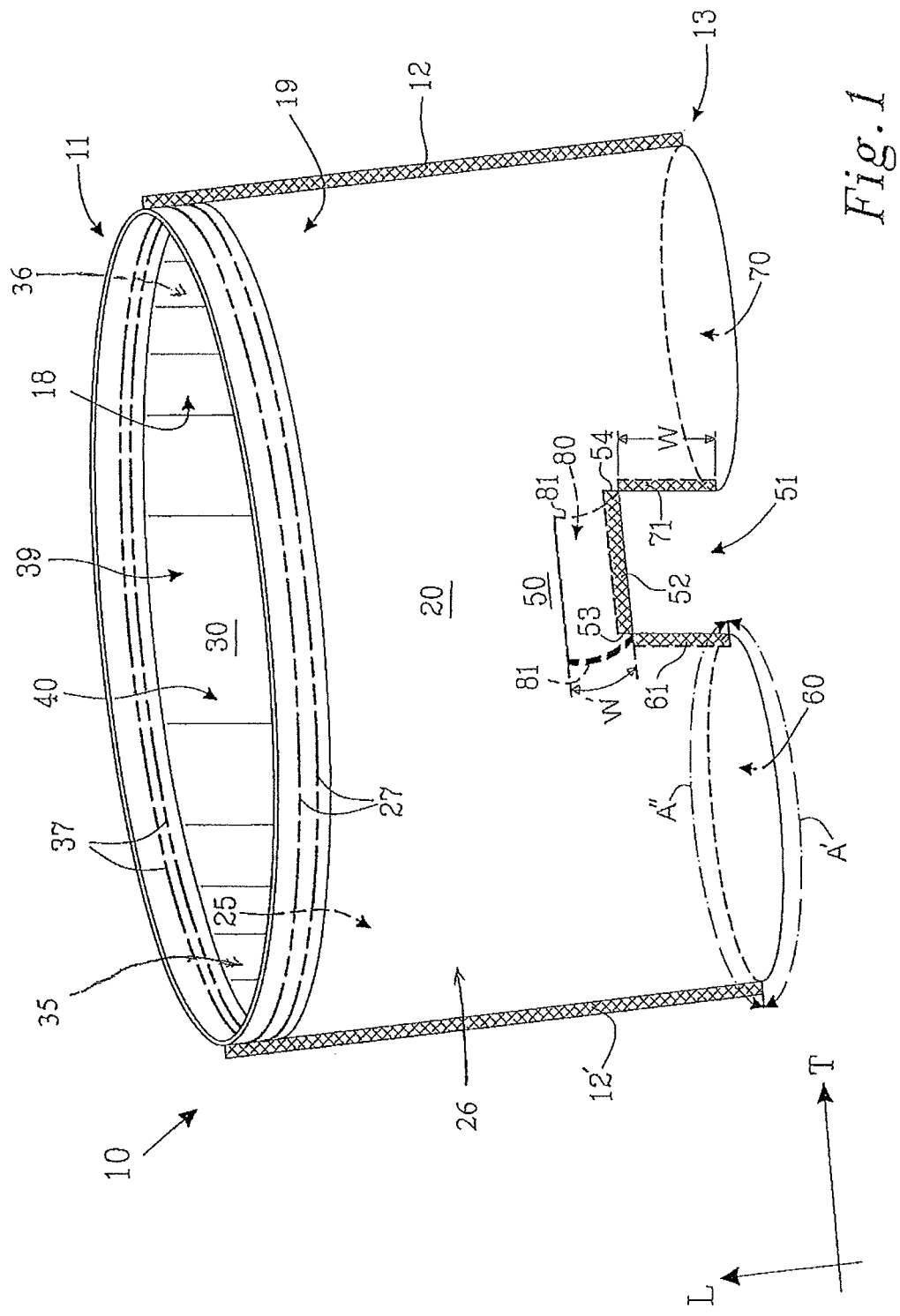
FIG. 1 shows a pant-type article according to an embodiment of the invention.
Figure 2:
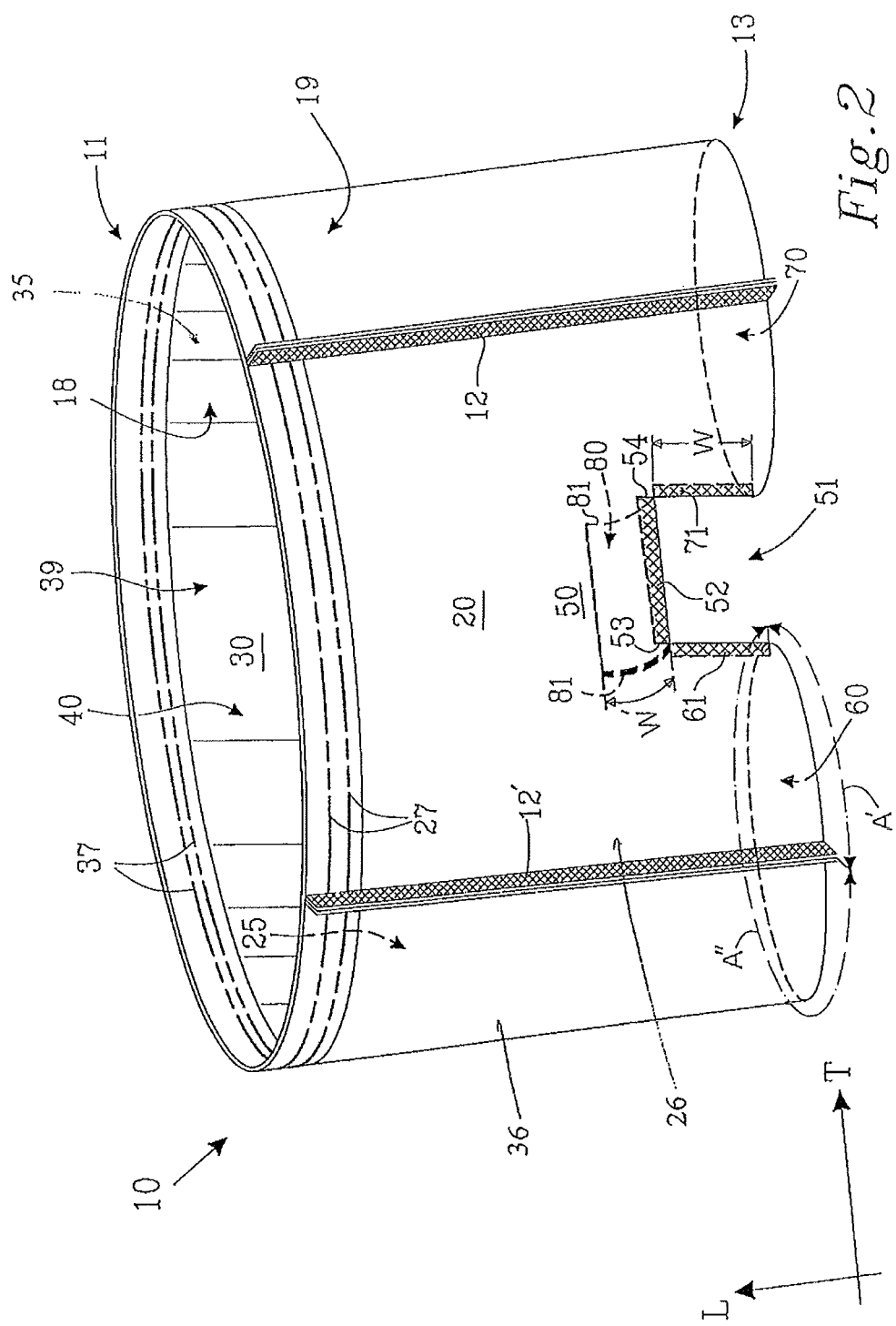
FIG. 2 shows an alternative embodiment of the pant-type article.
Figure 3:
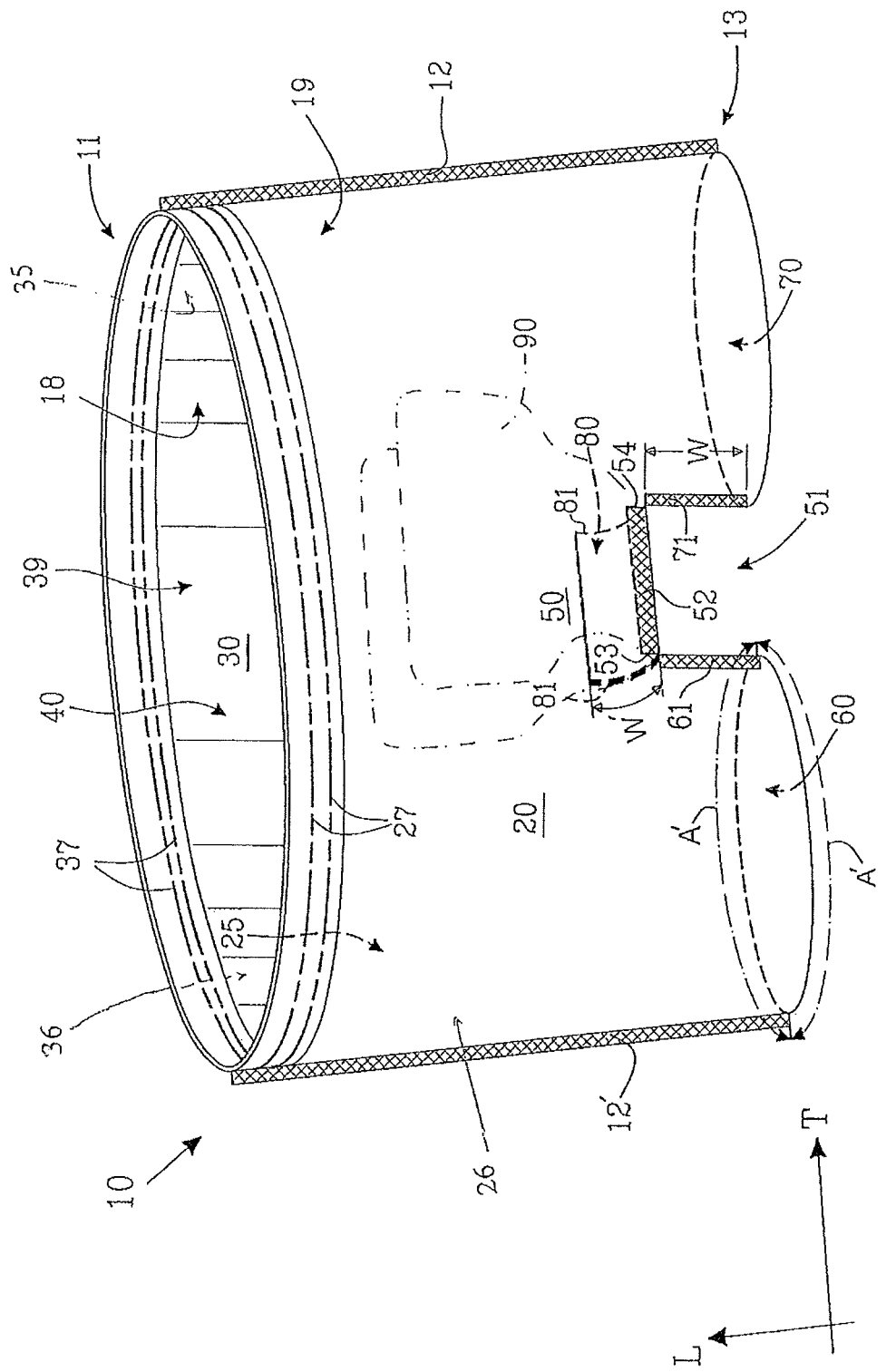
FIG. 3 shows a pant-type article according to another embodiment, being an absorbent pant-type article

The present disclosure relates to a pant-type article 10, as shown in FIGS. 1-3. The term "pant-type article" encompasses regular pants, protective pants and absorbent pants. The term "pant-type article" and "pants" are used interchangeably in this specification. Regular pants (underwear) are generally made of natural or synthetic woven fabric (e.g. cotton), and are designed to be washed and re-used regularly. Protective pants are pants which are substantially impermeable to liquids. As such protective pants typically include at least one layer of liquid-impermeable material, e.g. a plastic film or nonwoven material. In particular embodiments, protective pants are breathable—i.e. they allow the passage of gas and vapour. Protective pants may be used alone, or in combination with one or more absorbent bodies. Protective pants may be washable and re-usable, or may be disposable.

An example of a protective pants/absorbent insert combination is provided in e.g. U.S. Pat. No. 6,193,702.

In a particular embodiment, the pant-type article 10 is a pair of absorbent pants, as shown in FIG. 3. Absorbent pants are used for the uptake, storage and management of bodily exudate, such as urine, faeces and/or menses. As such, it typically includes one or more absorbent members 90 located in the interior 18 of the article 10. The absorbent member(s) 90 are arranged at least in the crotch region 50 of the pants 10, which is that portion which is located between the legs of the wearer when the pants 10 are worn, and may also extend somewhat into the front and rear portions of the pant-type article 10. In particular embodiments, absorbent pants are disposable—i.e. they are not meant to be cleaned and re-used.

The pant-type article 10 includes a first panel 20 and a second panel 30. For absorbent pant-type articles, the panels 20, 30 are suitably constituted by the backsheet 39, and—as such—may include any material described as suitable for use as backsheet 39. For regular pants (underwear), the panels 20, 30 may include a woven material. In particular embodiments, the material of the panels 20, 30 is elastic, in at least the transverse direction. An elastic material is defined as a material having a permanent elongation after relaxation of less than 10% after the material has been subjected to an elongation of 30% in the elasticity test specified herein. In particular embodiments, the material of the panels 20, 30 is liquid-impermeable, yet should be gas-permeable. Other layers of material may be laminated to the backsheet 39 in the panels 20, 30 as desired.

The panels 20, 30 have an extension in the transverse direction (T), as shown in FIGS. 1-3. The panels 20, 30 suitably extend in the transverse direction a distance of between 15 and 50 cm in an unstretched state. The panels 20, 30 also have an extension in the longitudinal direction (L), which, in certain embodiments, lies between 18 and 60 cm in an unstretched state. Suitably, the edges of the panels 20, 30 are straight and parallel to one another. Accordingly, the panels 20, 30 are suitably square or rectangular. As shown in FIGS. 1-3, the panels 20, 30 have inside faces 25, 35 arranged to face inwards in the article 10 and outside faces 26, 36 arranged to face outwards.

Either of the first 20 or second 30 panels may constitute the front or rear of the pant-type article 10.

The first 20 and second 30 panels are joined by first and second side seams 12, 12' to form a waist opening 40 at a first transverse end 11 of said article 10. The waist opening 40 is that part of the pant-type article 10 which encircles the waist of the wearer when the article is being worn. Joining in the side seams 12, 12' can take place by means of adhesive, heat or ultrasonic welding or any other method known in the art.

Elastic members 27, 37 may be located about the waist opening 40 to hold the article in place about the wearer's waist. In particular embodiments, the elastic members 27, 37 constitute a continuous band of elastic which encircles the waist opening 40 of the article 10, as shown in FIGS. 1-3. However, it may be acceptable that only a portion of the waist opening 40 includes elastic members. Alternatively, or additionally, the material of the panels 20, 30 may itself be an elastic material. Suitable elastic materials include elastic nonwoven materials, elastic woven materials or elastic films and laminates thereof. In particular embodiments, the material of the panels 20, 30 is a laminate of an elastic film between two nonwoven materials, or elastic threads between two nonwoven materials. If the material includes a film, the film is preferably breathable.

As shown in FIGS. 1-3, first and second panels 20, 30 are also joined by a crotch region joint 51 in the crotch region 50 spaced from said waist opening 40. The crotch region joint 51 joins the panels 20, 30 of the article together to thereby form a pair of leg openings 60, 70 at a second transverse end 13 of the article 10, on either side of the crotch region joint 51. Joining to form the crotch region joint 51 can take place by means of adhesive, heat or ultrasonic welding or any other method known in the art. Joining may even take place by stitching, although stitching is less suitable for rapid continuous production of articles, and for articles in which liquid-impermeability is important.

The shape and arrangement of the crotch region joint 51 allows the particular shape of the pant-type article 10 to be achieved. The crotch region joint 51 includes a crotch seam 52 extending substantially perpendicular to said first and second side seams 12, 12' and spaced therefrom. The crotch seam 52 has a first end 53 and a second end 54. The crotch seam 52 forms the crotch region joint 51 in the uppermost portion thereof. It is important that the crotch seam is linear and substantially perpendicular to the side seams 12, 12', as can be understood from the particular manufacturing methods described in the following. The crotch seam 52 is to be located between the wearer's legs when the pant is worn, so its length suitably lies between 3 and 18 cm.

The crotch region joint 51 further includes a first inner leg seam 61 extending a first distance (W) from said first end 53 of said crotch seam 52 to the second transverse end 13 of said pant-type article 10. The crotch region joint 51 also comprises a second inner leg seam 71 extending said first distance (W) from said second end 54 of said crotch seam 52 to the second transverse end 13 of said article 10. The distance (W) corresponds to the length of the legs of the boxer shorts, as measured from the crotch seam 52, on the inside of the leg to the end of the leg openings. Extension distance (W) can be varied as desired, depending on process parameters and the particular leg length one wishes to provide, yet typically lies between 3 and 18 cm (see FIG. 1).

Therefore, the crotch region joint 51 includes first inner leg seam 61, crotch seam 52 and second inner leg seam 71.

The first 61 and second 71 inner leg seams are typically straight parallel lines. However, if desired, the inner leg seams may be curved, in a direction towards the center of the panels 20, 30. Angled and curved slits may be used to provide a pant-type article 10 which has profiled legs, which seal closely about the thighs of the wearer. When the inner leg seams are straight, they typically extend perpendicular to the second transverse end 13 of the pant-type article 10. In effect, the first and second inner leg seams 61, 71 are suitably arranged parallel to the side seams 12, 12' of the article 10.

However, the inner leg seams 61, 71 may also be angled relative to the second transverse end 13 (i.e. they are not parallel to one another). In a particular embodiment, the inner leg seams 61, 71 are further from one another at the point at which they meet the crotch seam 52 than at the leg openings 60, 70. Inner leg seams 61, 71 which are angled can provide pant-type articles having legs which have a greater width at the leg openings 60, 70 than at the crotch seam 52. This feature is useful, as the diameter of the wearer's legs tends to be greater at a point on the thigh than in the crotch, and good fit can thus be obtained.

As shown in FIGS. 1-3, the article 10 also has an interior 18 and an exterior 19. The article 10 includes a crotch flap 80 located in the interior of said article 10. The crotch flap 80 includes material of said first and second panels 20, 30. The crotch flap 80 extends from said crotch seam 52 by a second distance (W') substantially equal to said first distance (W). In this way, material of the panels 20, 30 in the crotch flap is inverted inside the pant-type article 10, and no material is wasted during manufacture.

The first and second panels 20, 30 may be joined to one another in the crotch flap 80. Suitably, the first and second panels 20, 30 are joined to one another in the crotch flap 80 at least along longitudinal edges 81 thereof. This may be achieved during manufacture by cutting first and second panels 20, 30 such that one cutting line lies within each of the first 61 and the second 71 inner leg seams. In this way, a portion of each inner leg seam 61, 71 remains on the crotch flap 80, at the longitudinal edges 80 thereof. As an alternative, the first and second panels 20, 30 are joined to one another in the crotch flap 80 across substantially the entire crotch flap 80.

The crotch flap 80 may be loose inside the article 10 (i.e. it is not joined to any other component of the article 10). This is a possible arrangement for the absorbent pant-type article 10 illustrated in FIG. 3, as the absorbent core 90 will cover the crotch flap 80. However, in one embodiment, the crotch flap 80 may also be joined to the inside face 25, 35 of said first 20 or said second 30 panel. This arrangement provides added strength in the crotch region 50, and may be achieved during manufacture by introducing an extra joining step within the folding steps detailed below.

The pant-type article 10 has advantages over those known from in the field. Notably, the material of the first and second panels 20, 30 is doubled in the crotch region 50, which leads to improved leak-protection. Additionally, the crotch flap 80 in the crotch region 50 can provide improved mechanical strength, particularly against shear forces, as joining occurs over a relatively large area, and the material is doubled in the crotch region 50. This is particularly important in the crotch region 50 of pant-type articles, as this region is subjected to a range of forces between the wearer's legs, such as those forces imparted by activities such as walking or running, or when the article is put on or removed. Furthermore, the pant-type article 10 avoids large, bulky seams or welds in the crotch region 50, thus providing greater comfort. The narrow seam obtained in e.g. US 2003/0115660 can form a sharp edge which cuts, chafes or otherwise irritates the wearer's skin.

If desired, the leg openings 60, 70 of the pant-type article 10 may include one or more elastic members located in the second transverse end 13 of said article 10 (not shown). These leg elastics serve to seal the leg openings about the thighs of the wearer.

In FIG. 1, the distance between the first and second inner leg seams 61, 71 and the side seams 12, 12' in the first panel 20 (shown as distance A' in FIG. 1) is the same as the corresponding distance in the second panel 30 (shown as distance A" in FIG. 1). This allows simple, easy construction of the pant-type article 10.

FIG. 2 shows an embodiment in which the distance (A') between the first and second inner leg seams 61, 71 and the side seams 12, 12' in the first panel 20 is smaller than the corresponding distance (A") in the second panel 30. The opposite situation is also possible. The situation illustrated in FIG. 2 may be achieved by manufacturing the panels 20, 30 with different dimensions; alternatively, the first panel 20 may be joined to the second panel 30 at the side seams 12, 12' in a stretched condition. The embodiment shown in FIG. 2 allows the side seams 12, 12' to be located more towards the front of the article 10, which can reduce discomfort due to chafing of the side seams 12, 12', and allow flexibility in the appearance of the article 10.

If the pant-type article is to be an absorbent pant, as illustrated in FIG. 3, it additionally includes an absorbent member 90 located on the inside of the article 10. A typical absorbent pant construction therefore includes at least an absorbent member 90 and a breathable backsheet 39. Optionally, a liquid-permeable topsheet is also present.

The backsheet 39 of the article 10 is the layer which lies furthest from the wearer's body when the article is in use, and may constitute the outermost layer of the pant-type article 10. To protect the wearer's garments from soiling, it should be liquid-impermeable at least in the region which overlaps with the absorbent member 90. The backsheet should be gas-permeable to allow air and vapour to pass in and out of the article so that the warm, damp conditions which can arise in a diaper are reduced. Typically, the backsheet 39 is a laminate including plastic films and nonwoven materials, or elastic threads between two nonwoven materials. Examples of breathable backsheet materials are porous polymeric films, nonwoven laminates from spunbond and meltblown layers, laminates from porous polymeric films and nonwovens. The backsheet 39 may be different in different parts of the absorbent article 10, but should be liquid-impermeable at least in the region which overlaps with the absorbent member 90 (and in particular only in this region). The absorbent member 90 may have its own liquid-impermeable backsheet 39.

The absorbent member 90 of the article 10 acts to receive and contain liquid and other bodily exudates and can be of any conventional kind. As such, it typically includes absorbent material. Examples of commonly-occurring absorbent materials are cellulosic fluff pulp, tissue layers, highly-absorbent polymers (so called superabsorbents), absorbent foam materials, absorbent nonwoven materials or the like. It is common to combine cellulosic fluff pulp with superabsorbents in an absorbent body. It is also common to have absorbent members 90 including layers of different material with different properties with respect to liquid receiving capacity, liquid distribution capacity and storage capacity. The thin absorbent members 90, which are common in for example baby diapers and incontinence guards, often include a compressed mixed or layered structure of cellulosic fluff pulp and superabsorbent. The size and absorbent capacity of the absorbent member 90 may be varied to be suited for different uses such as for infants or for incontinent adults.

The absorbent member 90 may include one or more layers which are designed to improve the handling of bodily waste. Such layers are designed to receive a large amount of liquid in a short space of time and distribute it evenly across the absorbent member 90. They may include so-called transfer, distribution, surge or acquisition layers, and are usually located between the topsheet 16 and the absorbent member 90.

As mentioned above, the pant-type article 10 may include a liquid-permeable topsheet. The topsheet of the article 10 is the layer which lies in contact with the wearer's body when the article is in use. As such, it should be soft, non-irritating and comfortable against the skin, and bodily fluid should be able to pass through it without hindrance. The topsheet can consist of a nonwoven material, e.g. spunbond, meltblown, carded, hydroentangled, wetlaid etc. Suitable nonwoven materials can be composed of natural fibers, such as wood-pulp or cotton fibres, manmade fibres, such as polyester, polyethylene, polypropylene, viscose etc. or from a mixture of natural and manmade fibres. The topsheet may further be composed of tow fibres, which may be bonded to each other in a bonding pattern, as e.g. disclosed in EP-A-1 035 818. Further examples of materials suitable for topsheets are porous foams, apertured plastic films etc. The topsheet may be different in different parts of the absorbent pant-type article 10. The absorbent member 90 may have its own topsheet.

The topsheet and backsheet 39 generally have a similar extension within the article 10, while the absorbent member 90 has an extension which is somewhat smaller. The topsheet and backsheet 39 may be joined to one another around the periphery of the absorbent member 90, so that the absorbent member 90 is enclosed within the envelope formed by the topsheet and the backsheet 39. The topsheet and backsheet 39 may be joined to one another by any means common in the art, e.g. ultrasonic welding, thermal welding or gluing. The topsheet and backsheet 39 may also enclose the absorbent member 90, as a so-called "core packet", which is then applied to the material of the pant-type article 10.

Figure 4:
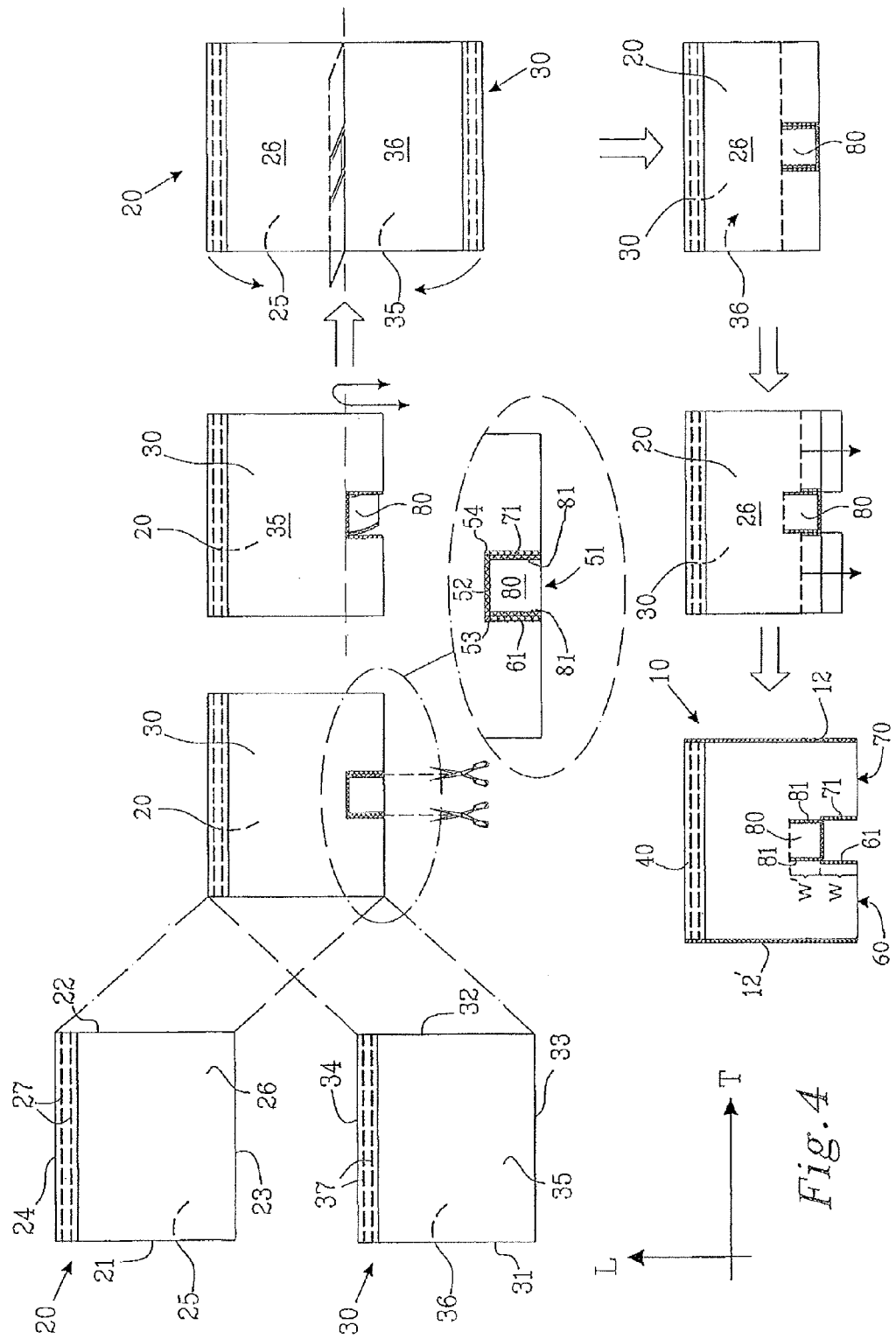
FIG. 4 illustrates a first method suitable for manufacturing a pant-type article.

FIG. 4 shows one method for manufacturing a pant-type article.

A first panel 20 is provided (FIG. 4). The first panel 20 has an extension in the transverse direction (T) and is defined by first and second longitudinal edges (21, 22) and has an extension in the longitudinal direction (L) and is defined by first (23) and second (24) transverse edges. The first panel 20 also has opposing inside 25 and outside 26 faces.

Similarly, a second panel 30 is also provided (FIG. 4). The second panel 30 also has an extension in the transverse direction (T) and is defined by first and second longitudinal edges 31, 32 and has an extension in the longitudinal direction (L) and is defined by first 33 and second 34 transverse edges. The second panel 30 also has opposing inside 35 and outside 36 faces.

The material used for the first and second panels 20, 30, and the panels themselves are described in more detail above, in relation to the pant-type article 10.

The first 20 and second 30 panels are brought to overlap with one another, as shown in FIG. 4, such that the outside faces 26, 36 of said panels 20, 30 face one another (i.e. in a back-to-back relationship). This arrangement of the panels 20, 30 is important, as it is the first step in forming the particular structure of the pant-type article 10.

First and second panels 20, 30 are joined to form a crotch seam 52, as shown. The crotch seam 52 extends substantially parallel to the first 23, 33 and second 24, 34 transverse edges of the panels 20, 30 and is spaced therefrom. Joining can take place by means of adhesive, heat or ultrasonic welding or any other method known in the art.

First and second panels 20, 30 are also joined to form a first inner leg seam 61 extending a first distance (W) from a first end 53 of the crotch seam 52 to a first transverse edge 23, 33 of the first and second panels 20, 30. This is also illustrated in FIG. 4. Similarly, first and second panels 20, 30 are joined to form a second inner leg seam 71 extending said first distance (W) from a second end 54 of said crotch seam 52 to a first transverse edge 23, 33 of said first and second panels 20, 30. As above, joining in the inner leg seams 61, 71 can take place by means of adhesive, heat or ultrasonic welding or any other method known in the art. In this way, the crotch region joint 51 shown in FIG. 4 is constructed, and includes first inner leg seam 61, crotch seam 52 and second inner leg seam 71.

The joining of the crotch seam 52, and inner leg seams 61, 71 may be carried out essentially simultaneously in the same joining step. The method may further include the step of joining first and second panels 20, 30 to one another in said crotch flap 80 at least along longitudinal edges 81 thereof. This may be achieved as set out below, in that first and second panels 20, 30 are cut such that one cutting line lies within each of the first 61 and the second 71 inner leg seam. A portion of the join constituting the inner leg seam 61, 71 therefore remains on the crotch flap 80. It is even possible to join the first and second panels 20, 30 to one another across substantially the entire area of the crotch flap 80.

First and second panels 20, 30 are then cut along two lines, each of which extends from the first transverse edge 23, 33 of the first and second panels 20, 30 to the crotch seam 52 so as to define a crotch flap 80. The cutting lines lie inwardly of the inner leg seams 61, 71 in the panels 20, 30. Suitably first and second panels 20, 30 are cut such that one cutting line lies within each of the first 61 and the second 71 inner leg seam. Cuts in the first and second panels 20, 30 penetrate completely through the thickness of the material in which they are formed. Cutting may be carried out using any method common in the art, e.g. cutting with an RDC (rotary die cut), water jets or a laser, or even thermal or ultrasonic melting. Cuts may be made parallel, or non-parallel. In particular, cuts may be made such that the inner leg seams 61, 71 are further from one another at the point at which they meet the crotch seam 52 than at the leg openings 60, 70.

The co joined first 20 and second 30 panels are then folded along the crotch seam 52, so that the inside faces 25, 35 of said first and second panels 20, 30 face one another.

This is shown in FIG. 4. Folding may take place of both panels simultaneously, or one panel 20, 30 may be folded before the other. In effect, the entire article 10 is turned inside-out, with the exception of the crotch flap 80, which is prevented from being inverted by the crotch seam 52. At this point, the material which is to form the leg openings 60, 70, between the fold line and the first transverse edges 23, 33, is also not inverted (see FIG. 5).

The inside faces 25, 35 of the first and second panels 20, 30 thus become oriented in a face-to-face relationship. The material of the panels which is located between the crotch seam 52 and the first transverse edges 23, 33 of the panels therefore becomes folded between the inside faces 25, 35 of the panels 20, 30.

The co joined first 20 and second 30 panels are then inverted in the region between the inner leg seams 61, 71 and respective longitudinal edges 21, 22, 31, 32 of the panels 20, 30 to form leg openings 60, 70. This is shown in FIG. 4. Inversion of the panels 20, 30 may be carried out by mechanical means (e.g. arms or rotors which invert the panels) or even an apparatus which blows air between the first 20 and second 30 panels, thus inverting them. The shape of the pant-type article 10 is established at this point.

First 20 and second 30 panels are then joined together along first and second longitudinal edges 21, 22, 31, 32 to define side seams 12, 12' of the pant-type article. As above, joining in the side seams 12, 12' can take place by means of adhesive, heat or ultrasonic welding or any other method known in the art. A pant-type article 10 is provided.

The steps of the method illustrated in FIG. 4 are preferably carried out in the order set out above. However, variations in the sequence of steps can be performed as desired by the skilled person, provided that the resulting method allows the formation of the pant-type article 10. Generally, steps involving joining regions of the panels 20, 30 cannot take place until after the panels 20, 30 have been brought together in the appropriate configuration, and steps involving folding must take place at least after the panels 20, 30 have been joined via the crotch seam 52.

The steps of cutting the first 20 and second panels 30 may take place before or after the steps of joining the panels 20, 30 together via the crotch seam 52 and/or first and second inner leg seams 61, 71. In other words, the panels 20, 30 may be cut, then joined; or joined, then cut. It is, however, important that cuts are introduced before the first and second panels 20, 30 are folded. Cuts may even be introduced to each panel separately, before the panels are brought to overlap each other, although this is a less preferred option.

Secondly, the step of joining the first 20 and second 30 panels together along the inner leg seams 61, 71 may take place at any point in the process after the first and second panels 20, 30 have been brought together.

If the crotch flap 80 is to be joined to the inside face 25, 35 of the first 20 or said second 30 panel of the pant-type article 10, the manufacturing method may further include a step of joining said crotch flap 80 to the inside face 25, 35 of said first 20 or said second 30 panel. This step should preferably be carried out during the folding of the co joined first 20 and second 30 panels, but before the panels 20, 30 lie completely in a face-to-face manner. For instance, the first panel 20 might first be folded 180°, the crotch flap 80 can be joined to this panel, then the second panel 30 may be folded 180° to lie face-to-face with the first panel 20. As an alternative, the crotch flap 80 may be folded 180° and joined to the inside face 25, 35 of one of the panels 20, 30, before the other of the panels 20, 30 is folded.

The method illustrated may additionally include the step of fixing at least one elastic member 27, 37 adjacent at least a portion of the second transverse edge 24, 34 of at least one of the first and second panels 20, 30. Fixing elastic members 27, 37 may take place at any point during the method, but is most suitably carried out before first and second panels 20, 30 are joined together. Most preferably, elastic members 27, 37 are fixed adjacent the second transverse edges 24, 34 before the panels 20, 30 are cut. This is shown in FIG. 4.

Figure 5:
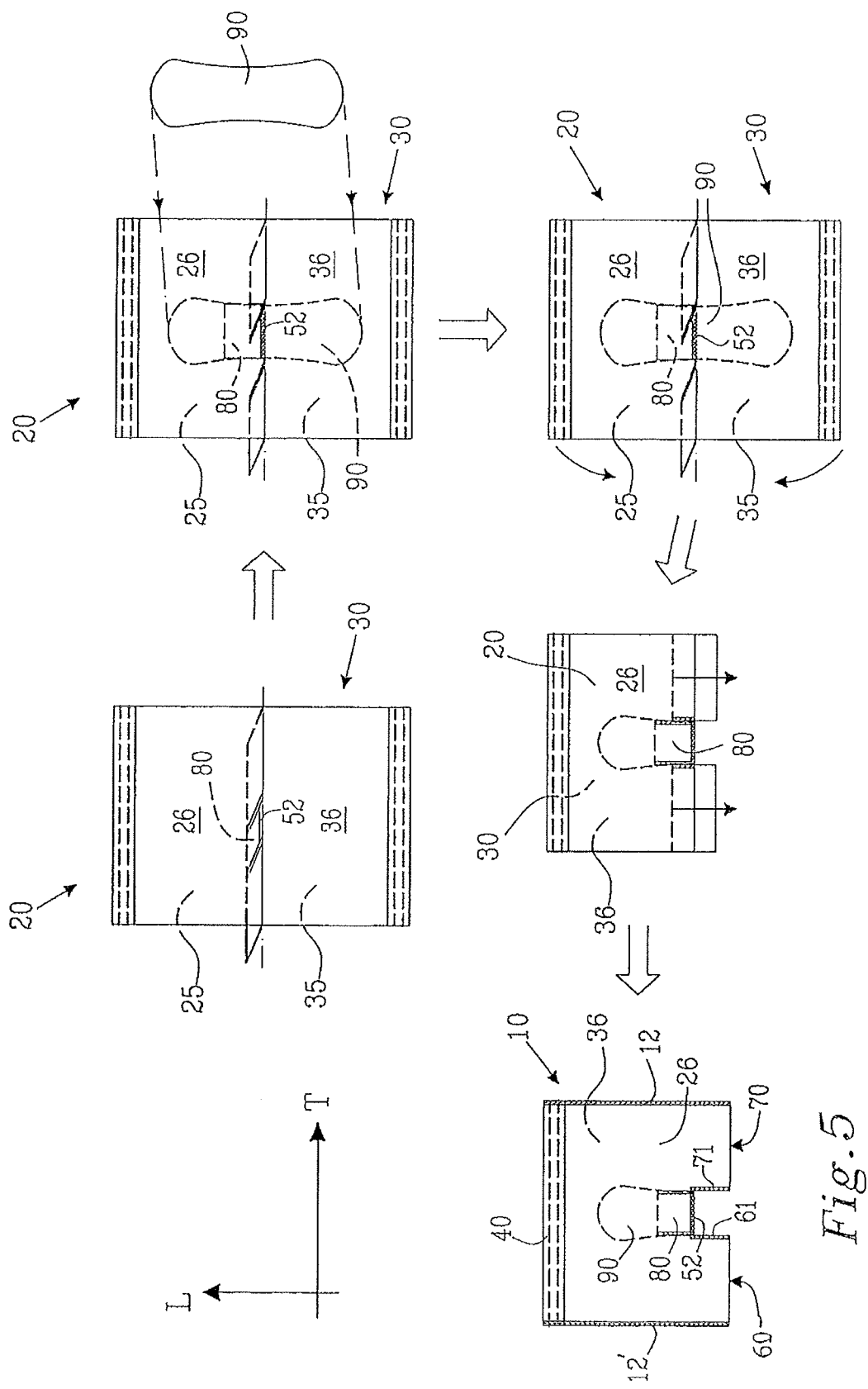
FIG. 5 illustrates additional steps which may be present in the method of FIG. 4, for making an absorbent pant-type article.

To form an absorbent pant-type article (including an absorbent member 90), the manufacturing method may further include the step of incorporating an absorbent member 90 in the interior 18 of the article 10, at least in the crotch region 50 thereof. The most effective way of incorporating an absorbent member 90 is to divide the step of folding the co-joined panels 20, 30 into a number of steps, as illustrated in FIG. 5. Other ways of incorporating the absorbent member 90 may also be possible, e.g. joining the absorbent member 90 to one panel prior to carrying out the method.

FIG. 5 shows that, firstly, the second 30 panel has been folded 180° along the crotch seam 52. The co joined panels are thus "opened" and lie essentially flat at this point. If desired, the crotch flap 80 can be joined to the inside face 25, 35 of the first or second panels 20, 30 at this point, as described above.

An absorbent member 90 is then joined to the first 20 and/or second 30 panels on the inside faces 25, 35 of at least one of said panels 20, 30. This takes place while the panels 20, 30 are in the "opened" form. Depending on the nature of the article 10, the absorbent member 90 can be joined to one or both panels 20, 30. For instance, if an absorbent article 10 is only meant for the containment of urine, it may be sufficient that the absorbent member 90 is located in and joined to only one panel 20, 30. Preferably, however, the absorbent member 90 is joined to both panels 20, 30. Joining of the absorbent member 90 should not interfere with subsequent joining or folding steps—if necessary, the absorbent member 90 should therefore only overlap the crotch region 50 and not the adjacent leg openings 60, 70.

After the absorbent member 90 has been joined to the first and/or second panels 20, 30, the first panel 20 is folded another 180° along the crotch seam 52 so that the inside faces 25, 35 of said first and second panels 20, 30 become oriented in a face-to-face relationship with the absorbent member 90 located therebetween. The absorbent member 90 therefore becomes sandwiched between the first and second panels 20, 30.

Naturally, the above method for manufacturing an absorbent pant-type article 10 can be carried out by folding the first panel 20 first, followed by application of the absorbent member 90 and another folding of the second panel 30. What is important is that the two panels are folded so as to lie 180° relative to one another prior to joining the absorbent member 90, and then folded a further 180° relative to one another after the absorbent member 90 has been joined.

After the absorbent member 90 has been joined to the absorbent article, a topsheet may also be applied on the wearer-facing surface of the article 10. The topsheet and backsheet 39 may be joined to one another around the periphery of the absorbent member 90, so that the absorbent member 90 is enclosed within the envelope formed by the topsheet and the backsheet 39. The topsheet and backsheet 39 may be joined to one another by any means common in the art, e.g. ultrasonic welding, thermal welding or gluing. The topsheet may also be wrapped about the absorbent member 90, as a so-called "core packet", and the entire core packet applied to the pant-type article 10 in one step.

For ease of manufacture, the absorbent member 90 is preferably no wider than the crotch seam 52 in the transverse direction. If the absorbent member 90 is, however, wider than the crotch seam 52 in the transverse direction, it is possible to fold the co joined first and second panels 20, 30 so that the inside faces 25, 35 adopt a face-to-face position. The leg openings 60, 70 are then inverted. The panels 20, 30 may then be opened up again, and the absorbent member 90 applied to the crotch region 50, without interfering with the leg openings 60, 70. The panels 20, 30 can then be folded closed again so that the absorbent member 90 is contained within the inside faces 25, 35 of the panels 20, 30, before side seams 12, 12' are formed.

A further aspect relates to a method for manufacturing a pant-type article 10 in a continuous process, well suited for high-volume, rapid production of such pant-type articles 10. All that is described above in relation to the first method in terms of e.g. materials, apparatus or specific methods, can also be applied to the second method, unless specifically stated. The second method is illustrated generally in FIG. 6.

First 200 and second 300 webs are provided. The term "web" is used to define a long length of material, which is typically transported and stored in roll form. When used in embodiments of the invention, the material is unwound and fed along a suitable apparatus in the so-called machine direction (MD), which is the length direction of the material. Each of said webs 200, 300 therefore has a major extension in the machine direction (MD) and is defined in the cross direction (CD) by first 201, 301 and second 202, 302 transverse edges. As per the first and second panels described above in relation to FIG. 4, the first web 200 has opposing inside 205 and outside 206 faces and the second web 300 also has opposing inside 305 and outside 306 faces. The first 200 and second 300 webs may be the same, or different. The material which includes the webs 200, 300 may be any material described above in connection with panels 20, 30.

First 200 and second 300 webs are brought to overlap with one another, such that their outside faces 206, 306 face one another (i.e. in a back-to-back relationship).

First and second webs 200, 300 are joined together at regular intervals in the machine direction to form a plurality of crotch seams 52 extending substantially in the machine direction (MD) and spaced from first and second transverse edges 201, 202, 301, 302 of each web 200, 300. As above, each crotch seam 52 has a first end 53 and a second end 54. Joining can take place by means of adhesive, heat or ultrasonic welding or any other method known in the art.

Figure 6:
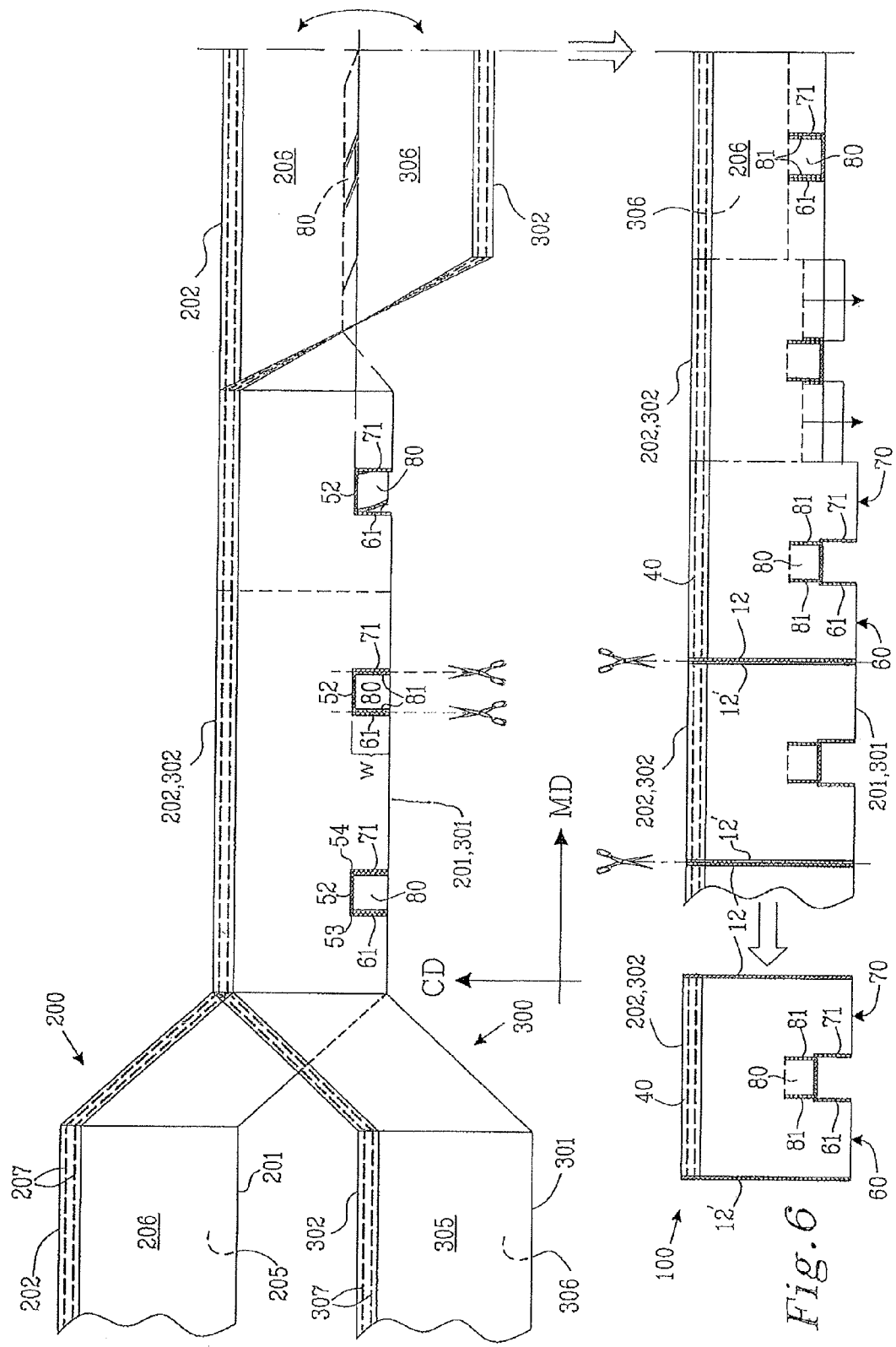
FIG. 6 illustrates a second method suitable for manufacturing a pant-type article, being a continuous process.

First and second webs 200, 300 are also joined together at regular intervals in the machine direction to form a plurality of first inner leg seams 61 extending a first distance (W) from the first end 53 of each crotch seam 52 to a first transverse edge 201, 301 of each web 200, 300. This is shown in FIG. 6. The intervals in the machine direction with which the first inner leg seams 61 are formed are the same intervals with which the crotch seams 52 are formed. Details of the nature and arrangement of the first inner leg seams 61 are as set out above. In particular, the distance (W) corresponds to the length of the inner leg seam 61 of the boxer shorts, as measured from the crotch seam 52, on the inside of the wearer's leg when in use.

Similarly, first and second webs 200, 300 are joined together at regular intervals in the machine direction to form a plurality of second inner leg seams 71 extending said first distance (W) from the second end 54 of each crotch seam 52 to a first transverse edge 201, 301 of each web 200, 300. Joining steps to form first inner leg seam 61, second inner leg seam 71 and crotch seam 52 may be carried out essentially simultaneously in the same joining step.

After this step, the webs 200, 300 are therefore joined by a crotch region joint 51 including first inner leg seam 61, crotch seam 52 and second inner leg seam 71. As above, joining in the inner leg seams 61, 71 or crotch seam 52 can take place by means of adhesive, heat or ultrasonic welding or any other method known in the art.

First and second webs 200, 300 are cut along pairs of cutting lines spaced at regular intervals in the machine direction. Each pair of lines extends from the first transverse edge 201, 301 of each web 200, 300 to each crotch seam 52 so as to define a plurality of crotch flaps 80 along the length of the webs 200, 300 in the machine direction MD. Suitably, first and second webs 200, 300 are cut such that one cutting line lies within each of the first 61 and the second 71 inner leg seams. Cuts may be made parallel, or non-parallel. In particular, cuts may be made such that the inner leg seams 61, 71 are further from one another at the point at which they meet the crotch seam 52 than at the leg openings 60, 70.

Co-joined first 200 and second 300 webs are then folded along the crotch seams 52; so that the inside faces 205, 305 of said first and second webs 200, 300 face one another. In effect, the webs are turned inside-out; however, the crotch flap 80 is prevented from being inverted by the crotch region joint 51.

The co-joined first 200 and second 300 webs are then inverted in the region between first 61 and second 71 inner leg seams to define leg openings 60, 70. This is shown in FIG. 6. Inversion of the webs 200, 300 may be carried out by mechanical means (e.g. arms or rotors which invert the webs) or even an apparatus which blows air between the first 200 and second 300 webs, thus inverting them. The shape of the pant-type article 10 is established at this point.

A joint is then made between the first 200 and the second 300 webs in said inverted region from the first 201, 301 to the second 202, 302 transverse edge of each web 200, 300. Side seams 12, 12' are thus provided. Joining may take place via any method known in the art.

The co joined first and second webs 200, 300 are cut within the leg seams 12, 12' from the first 201, 301 transverse edge to the second 202, 302 transverse edge of each web.

Cutting takes place within the side seam 12, 12', so that leg seams 12, 12' are present on either side of the cut, as shown in FIG. 6. Individual pant-type articles 10 are thus provided. Instead of cutting one side seam 12, 12' into two, alternatively, two joints may be present and a cut may be made between them, forming two separate leg seams 12, 12'.

The steps of the method illustrated in FIG. 6 are preferably carried out in the order set out above. The method has been illustrated and described in that articles 10 are joined to form crotch seams 52, inner leg seams 61, 51 and side seams 12, 12' first, and then separated from each other by cutting. This is the most preferred sequence, as it ensures that portions of the absorbent article 10 are joined in place before individual articles 10 are separated from each other. The risk for movement or undesired displacement of portions of the pant-type article 10 is therefore reduced. However, variations in the sequence of steps can be performed as desired by the skilled person, provided that the resulting method allows the formation of the pant-type article 10. Generally, steps involving joining the webs 200, 300 cannot take place until after the webs 200, 300 have been brought together in the appropriate configuration, and steps involving folding must take place at least after the webs 200, 300 have been joined.

Firstly, the steps of cutting the first 200 and second webs 300 may take place before or after the steps of joining the webs 200, 300 together via the crotch seams 52 and/or inner leg seams 61, 71. In other words, the webs 200, 300 may be cut, then joined; or joined, then cut. It is, however, important that cuts are introduced before the first and second webs 200, 300 are folded. Cuts may even be introduced to each web separately, before the webs are brought to overlap each other, although this is a less preferred option.

Secondly, the step of joining the first and second webs 200, 300 together along the inner leg seams 61, 71 may take place at any point in the process after the first and second webs 200, 300 have been brought together.

The method may further include the step of joining first and second webs 200, 300 to one another in each crotch flap 80, at least along longitudinal edges 81 thereof. This may be achieved as set out below, in that first and second webs 200, 300 are cut such that one cutting line lies within each of the first 61 and the second 71 inner leg seam. A portion of the join constituting the inner leg seam 61, 71 therefore remains on the crotch flap 80. It is even possible to join the first and second webs 200, 300 to one another across substantially the entire area of the crotch flap 80.

If the crotch flap 80 is to be joined to the inside face 205, 305 of the first 200 or said second 300 web of the pant-type article 10, the manufacturing method may further include a step of joining said crotch flap 80 to the inside face 205, 305 of said first 200 or said second 300 web. This step should be carried out during the folding of the co joined first 200 and second 300 webs, but before the webs 200, 300 lie completely in a face-to-face manner. For instance, the first web 200 might first be folded 180°, the crotch flap 80 can be joined to this web, then the second web 300 may be folded 180° to lie face-to-face with the first web 200. Alternatively, the crotch flap 80 may be folded 180° to lie against the inside face 205, 305 of the first or second webs 200, 300, joined to said inside face 205, 305, and then the web to which the crotch flap 80 is not joined is then folded so that the two inside faces 205, 305 of the webs 200, 300 lie in a face-to-face relationship.

Figure 7:
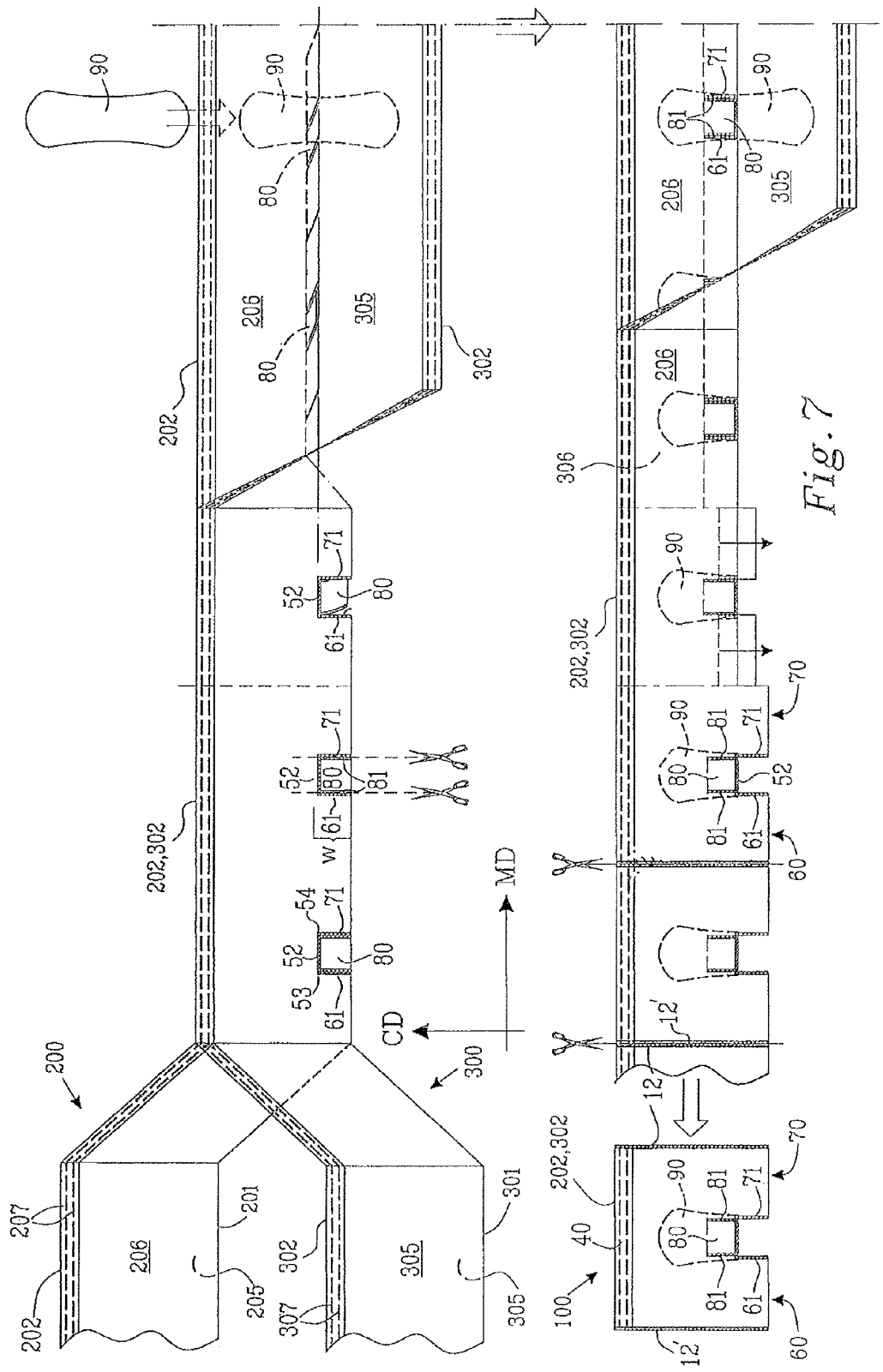
FIG. 7 illustrates additional steps which may be present in the method of FIG. 6, for making an absorbent pant-type article in a continuous process.

The second method may additionally include the step of fixing at least one elastic member 207, 307 adjacent at least a portion of the second transverse edge 202, 302 of at least one of the first 200 and second 300 webs. Fixing elastic members 207, 307 may take place at any point during the method, but is most suitably carried out before first and second webs 200, 300 are joined together. Most preferably, elastic members 207, 307 are fixed adjacent the second longitudinal edges 202, 302 before the webs 200, 300 are cut. Fixing elastic members 207, 307 is shown in FIGS. 6 and 7.

In order to form an absorbent pant-type article 100 (including an absorbent member 90) using the method illustrated in FIG. 6, the method further includes the step of incorporating an absorbent member 90 in the interior 18 of the article 10, at least in the crotch region 50 thereof. One suitable way of doing so is presented in FIG. 7, in which the step of folding the webs 200, 300 is separated into a number of individual steps. Other methods of incorporating an absorbent member 90 are also possible; e.g. applying absorbent members 90 to the individual webs 200, 300 before they are overlapped and joined.

Firstly, the first web 200 is folded 180° along the crotch seams 52. The co-joined webs are thus "opened" and lie essentially flat at this point. If desired, the crotch flap 80 can be joined to the inside face 205, 305 of the first or second webs 200, 300 at this point, as mentioned above.

An absorbent member 90 is then joined to the first 200 and/or second 300 webs, on the inside faces 205, 305 of at least one of said webs 200, 300. This takes place while the webs 200, 300 are in the "opened" form. Depending on the nature of the article 100, the absorbent member 90 can be joined to one or both webs 200, 300. For instance, if an absorbent article 100 is only meant for the containment of urine, it may be sufficient that the absorbent member 90 is located in and joined to only one web 200, 300. In particular embodiments, the absorbent member 90 is joined to both webs 200, 300. Joining of the absorbent member 90 should not interfere with subsequent joining or folding steps—in particular embodiments, the absorbent member 90 should therefore only overlap the crotch region 50 and not the adjacent leg openings 60, 70.

After the absorbent member 90 has been joined to the first and/or second webs 200, 300, the second web 300 is folded 180° along the crotch seam 52, so that the inside faces 205, 305 of said first and second webs 200, 300 become oriented in a face-to-face relationship with the absorbent member 90 located therebetween. The absorbent member 90 therefore becomes sandwiched between the first and second webs 200, 300.

Naturally, the above method for manufacturing an absorbent pant-type article 100 can be carried out by folding the second web 300 first, followed by application of the absorbent member 90 and folding of the first web 200. Alternatively, each web 200, 300 may be folded 90° and the absorbent member 90 applied.

If the absorbent member 90 is wider than the crotch seam 52 in the machine direction of the webs 200, 300, it is possible to first fold the co joined first and second webs 200, 300 so that the inside faces 205, 305 thereof adopt a face-to-face position. The leg openings 60, 70 are then inverted. The webs 200, 300 may then be opened up again, and the absorbent member 90 applied to the crotch region 50, without interfering with the leg openings 60, 70. The webs 200, 300 can then be folded closed again so that the absorbent member 90 is contained within the inside faces 205, 305 of the webs 200, 300, before side seams 12, 12' are formed.

After the absorbent member 90 has been joined to the absorbent article, a topsheet may also be applied on the wearer-facing surface of the article 100. The topsheet and backsheet 39 may be joined to one another around the periphery of the absorbent member 90, so that the absorbent member 90 is enclosed within the envelope formed by the topsheet and the backsheet 39. The topsheet and backsheet 39 may be joined to one another by any means common in the art, e.g. ultrasonic welding, thermal welding or gluing. The topsheet may also be wrapped about the absorbent member 90, as a so-called "core packet", and the entire core packet applied to the pant-type article 10 in one step.

The methods allow fast, cheap production of boxer-short articles in a side-by-side manner. Additionally—in that the webs 200, 300 or panels 20, 30 which constitute the articles may be different—the articles can be varied in a large number of ways.

Elasticity Test

The method measures how an elastic material behaves at cycles of repeated load and unload. The sample is stretched to a predetermined elongation and a cyclic movement between 0 and said predetermined elongation is performed. Desired load and unload forces are recorded. The permanent, i.e. remaining, elongation of the relaxed material is measure.

A tensile tester, Lloyd LRS, able to perform cyclic movements and equipped with a printer/plotter or software presentation is used. The sample is prepared by cutting it to a width of 25 mm and a length that is 20 mm longer than the distance between the clamps in the tensile tester.

The tensile tester is calibrated according to the apparatus instructions. The parameters needed for the test (unload and load forces) are adjusted to:

Crosshead speed: 500 mm/min
Clamp distance: 50 mm
Preload: 0.05N

The sample is placed in the clamps according to the marks and it is ensured that the sample is centred and fastened perpendicularly in the clamps. The tensile tester is started and three cycles between 0 and the predetermined elongation equal to the highest defined $1^{st}$ load are performed. After the last cycle, the sample is relaxed for 1 minute, then the permanent elongation is measured by stretching the sample until a force of 0.1N is detected and the elongation is read.

An elastic material is defined as a material having a permanent elongation after relaxation of less than 10% after the material has been subjected to an elongation of 30% in the test above. An elongation of 30% means an elongation to a length that is 30% longer than the initial length of the sample.

While the invention has been described with reference to a number of embodiments and Figures, it should not be considered as limited thereto. Rather, embodiments and features can be varied and combined at will by the skilled person, within the scope of the enclosed claims.

The invention claimed is:

1. A pant-type article comprising a first panel and a second panel, said first and second panels being joined by first and second side seams to form a waist opening at a first transverse end of said article, said first and second panels being further joined by a crotch region joint in a crotch region spaced from said waist opening to thereby form a pair of leg openings at a second transverse end of said article, wherein said crotch region joint comprises a crotch seam extending substantially perpendicular to said first and second side seams and spaced therefrom, wherein said crotch seam has a first end and a second end, wherein said crotch region joint further comprises a first inner leg seam extending a first distance from said first end of said crotch seam to said second transverse end of said article, wherein a second inner leg seam extends said first distance from said second end of said crotch seam to said second transverse end of said article, wherein said article has an interior and an exterior, the interior being defined as an area where the first panel faces the second panel other than the crotch region joint, wherein said article further comprises a crotch flap located in the interior of said article, said crotch flap comprising material of said first and second panels, and wherein said crotch flap extends within the interior of said article towards the waist opening and away from the crotch region joint by a second distance substantially equal to said first distance.

2. The pant-type article according to claim 1, wherein said first and second panels are joined in said crotch flap at least along longitudinal edges thereof.

3. The pant-type article according to claim 1, wherein said crotch flap is also joined to the inside face of said first or said second panel.

4. The pant-type article according to claim 1, additionally comprising an absorbent member located on the interior of the article, at least in the crotch region thereof.

5. The pant-type article according to claim 1, wherein the first and second inner leg seams are arranged parallel to the side seams of the article.

6. The pant-type article according to claim 1, wherein the first and second inner leg seams are not parallel to one another.

7. The pant-type article according to claim 5, wherein the first and second inner leg seams are further from one another at the point at which they meet the crotch seam than at the leg openings.

8. The pant-type article according to claim 1, wherein first and second longitudinal edges of the crotch flap are attached to an interior surface of either the first panel or the second panel, the first and second longitudinal edges extending in a direction that is parallel to the first and second side seams.

9. The pant-type article according to claim 1, wherein an upper edge of the crotch flap is attached to an interior surface of either the first panel or the second panel, the upper edge extending in a direction that is parallel to the waist opening.

* * * * *